US012741951B2

(12) United States Patent
Søndergaard et al.

(10) Patent No.: US 12,741,951 B2
(45) Date of Patent: Sep. 22, 2026

(54) CHLORANTRANILIPROLE PROCESS THROUGH USE OF A CRYSTAL INTERMEDIATE

(71) Applicants: FMC Corporation, Philadelphia, PA (US); FMC Agro Singapore Pte. Ltd., Singapore (SG)

(72) Inventors: Kåre Søndergaard, Holstebro (DK); Kim Lundkvist, Lemvig (DK); Jack K. Vinther, Holstebro (DK); Matthew Richard Oberholzer, Wilmington, DE (US); Erin Gallagher Demko, Wilmington, DE (US); Steven T. Booth, Wilmington, DE (US)

(73) Assignees: FMC CORPORATION, Philadelphia, PA (US); FMC IP TECHNOLOGY GMBH, Neuhausen (CH)

( * ) Notice: Subject to any disclaimer, the term of this patent is extended or adjusted under 35 U.S.C. 154(b) by 724 days.

(21) Appl. No.: 18/017,322

(22) PCT Filed: Jul. 22, 2021

(86) PCT No.: PCT/US2021/042679

§ 371 (c)(1),
(2) Date: Jan. 20, 2023

(87) PCT Pub. No.: WO2022/020540

PCT Pub. Date: Jan. 27, 2022

(65) Prior Publication Data

US 2023/0286939 A1 Sep. 14, 2023

Related U.S. Application Data

(60) Provisional application No. 63/055,446, filed on Jul. 23, 2020.

(51) Int. Cl.
*C07D 401/04* (2006.01)
*C07C 237/30* (2006.01)
*C07D 213/16* (2006.01)

(52) U.S. Cl.
CPC .......... *C07D 401/04* (2013.01); *C07C 237/30* (2013.01); *C07D 213/16* (2013.01); *C07B 2200/13* (2013.01)

(58) Field of Classification Search
CPC ................ C07D 401/04; C07D 213/16; C07C 237/30; C07B 2200/13
See application file for complete search history.

(56) References Cited

FOREIGN PATENT DOCUMENTS

WO 2020/117493 A1 6/2020

OTHER PUBLICATIONS

International Search Report of Corresponding PCT/US2021/042679 patent application.

*Primary Examiner* — Timothy R Rozof
(74) *Attorney, Agent, or Firm* — FMC CORPORATION

(57) ABSTRACT

Disclosed are three-component crystals comprising compounds of Formula II, compounds of Formula III and an amine base in an equimolar ratio (1:1:1). Also disclosed are methods for preparing the three-component crystals comprising compounds of Formula II, compounds of Formula III and an amine base in an equimolar ratio (1:1:1). Further disclosed are methods for the preparation of chlorantraniliprole using the three-component crystals of the disclosure.

7 Claims, No Drawings

CHLORANTRANILIPROLE PROCESS THROUGH USE OF A CRYSTAL INTERMEDIATE

CROSS-REFERENCE TO RELATED APPLICATIONS

This application claims the benefit of U.S. Provisional Application Nos. 63/055,446 filed Jul. 23, 2020, incorporated by reference herein in its entirety.

FIELD

This disclosure relates to three-component crystals including intermediates produced in the last step of the synthesis of chlorantraniliprole. This disclosure further relates to a method for preparing chlorantraniliprole using the three-component crystals of the disclosure.

BACKGROUND 3-bromo-1-(3-chloro-2-pyridinyl-1)-1H-pyrazole-5-carboxylic acid (Formula II) and 2-amino-5-chloro-N,3-dimethylbenzamide (Formula III)

Formula II

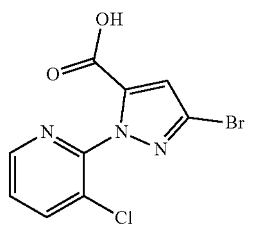

Formula III

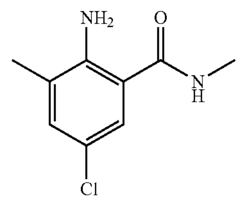

are key intermediates in the last step of the synthesis of compounds of chlorantraniliprole (Formula I).

Formula I

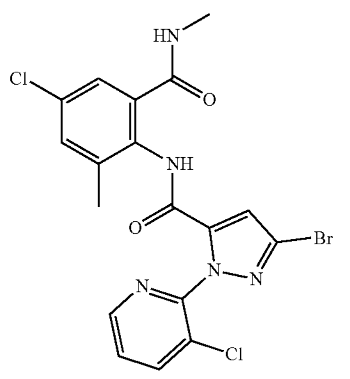

Conventional processes for the production of higher purity compounds of Formulas II and III generally involve recrystallization steps for both intermediates, individually, which generates more waste and yield loss. New methods of producing high purity compounds of Formulas II and III are needed.

SUMMARY

This disclosure is directed to a three-component crystal including (a) a compound of Formula II:

Formula II

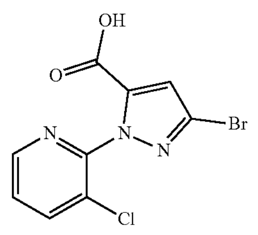

(b) a compound of Formula III; and

Formula III

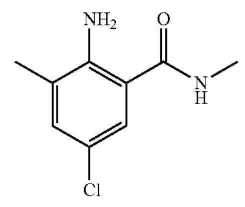

(c) an amine base, in an equimolar ratio (1:1:1).

This disclosure is further directed toward a method for the preparation of a three-component crystal including (a) a compound of Formula II:

Formula II

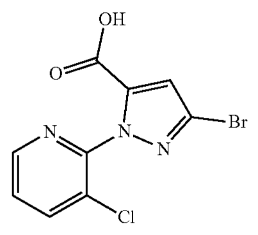

(b) a compound of Formula III; and

Formula III

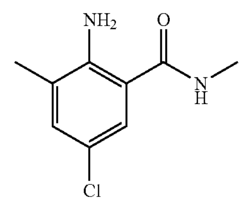

(e) an amine base, in an equimolar ratio (1:1:1), the method including the steps of:

(i) mixing the compound of Formula II, the compound of Formula III and the amine base in a polar aprotic solvent, and (ii) isolating the three-component crystals from the polar aprotic solvent.

This disclosure is further directed toward a method for the preparation of a compound of Formula I Formula I

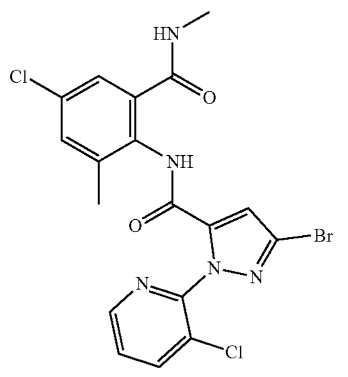

the method including the steps of:

(a) reacting a suspension of a three-component crystal including (i) a compound of Formula II:

Formula II

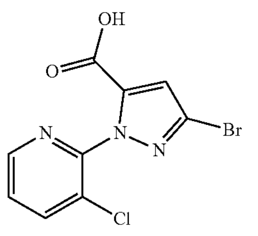

(ii) a compound of Formula III; and

Formula III

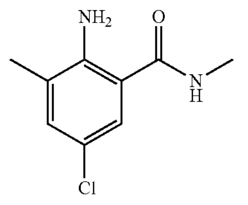

(iii) an amine base, in an equimolar ratio (1:1.:1) in an aprotic polar solvent with an acid activating agent, (b) allowing the coupling of acid activated compounds of Formulas II and III to proceed to the formation of the compound of Formula I, This disclosure is further directed toward a method for the preparation of a compound of Formula I Formula I

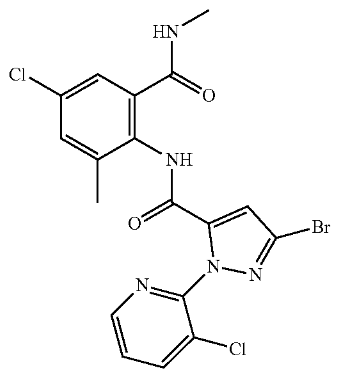

the method including the steps of:

(a) preparing a mixture including a compound of Formula II:

Formula II

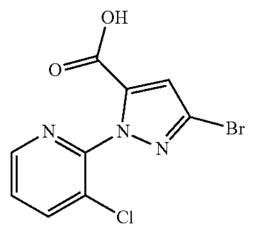

a compound of Formula III; and

Formula III

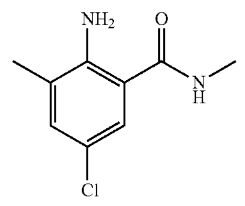

an amine base and a polar aprotic solvent, (b) gradually adding an acid activating agent to the mixture; and (c) allowing the coupling of acid activated compounds of Formulas II and III to proceed to the formation of the compound of Formula I;

wherein seeding material of the compound of Formula I is (i) added when preparing the mixture of step (a), (ii) added to the mixture before the acid activating agent has been added in step (b); or (iii) added during addition of the activating agent in step (b).

DETAILED DESCRIPTION

As used herein, the terms “comprises,” “comprising,” “includes,” “including,” “has,” “having,” “contains”, “containing,” “characterized by” or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claims. The term "consisting essentially of" occupies a middle ground between "comprising" and "consisting of".

Where applicants have defined an embodiment or a portion thereof with an open-ended term such as "comprising," it should be readily understood that (unless otherwise stated) the description should be interpreted to also describe such an embodiment using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the disclosure are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used herein, "amine base" refers to organic bases and salts thereof including primary, secondary and tertiary amines. Examples include substituted amines, cyclic amines, naturally-occurring amines and the like, such as pyridine bases (e.g., 3-picoline), N,N'-dibenzylethylenediamine, diethylamine, 2-diethylaminoethanol, 2-dimethylaminoethanol, ethanolamine, ethylenediamine, N-ethylmorpholine, N-ethylpiperidine, isopropylainine, morpholine, piperazine, piperidine, triethylamine, trimethylamine, tripropylamine, tromethamine, and the like.

As used herein, "aprotic solvent" refers to any solvent not having a proton-donating ability. Examples include, without any limitation, acetonitrile, 2-methyltetrahydrofuran, tetrahydrofaran, ethyl acetate, propyl acetate (e.g., isopropyl acetate), acetone, dimethylsulfoxide, N,N-dimethylformamide, N,N-dimethylacetamide, N-methylpyrrolidone, hexamethylphosphoramide, and propylene carbonate.

As used herein, the term "polar aprotic solvent" refers to an aprotic solvent that is a polar solvent. Examples include, without any limitation, acetonitrile, N,N-dimethylformamide, and the like.

As used herein, the term "acid-activating agent" refers to a reactant that facilitates coupling of a carboxylic acid compound with an anthranilamide. Examples include, without any limitation, compounds of the general formula $R^1S(O)_2Cl$ (Formula IV) wherein $R^1$ is a carbon based radical, such as $C_1$-$C_4$ alkyl, $C_1$-$C_2$ haloalkyl, or phenyl optionally substituted with 1-3 substituents selected from the group consisting of halogen, $C_1$-$C_3$ alkyl and nitro. Examples further include, without any limitation, methanesulfonyl chloride ($R^1$ is $CH_3$), propanesulfonyl chloride ($R^1$ is $(CH_2)_2CH_3$), benzenesulfonyl chloride ($R^1$ is Ph), and p-toluenesulfonyl chloride ($R^1$ is 4—$CH_3$—Ph).

As used herein, the term "approximately" refers to ±5%, ±2.5%, ±1%, ±0.5%, ±0.1%, or ±0.05% of a referenced basis, such as for instance and without limitation, population %, w/w %, w/v %, v/v %, or particle size.

As used herein, the term "unit cell dimension" is referred to as a lattice parameter, and the unit-cell is the simplest minimum repeating unit and defined by three crystallographic axes, the lengths of the three vectors (a, b, c) and the inter-axial angles (α, β, γ).

Embodiments of the present disclosure as described in the Summary include, but are not limited to those described below.

Embodiment A. A three-component crystal comprising a compound of Formula II, a compound of Formula III and an amine base in an approximately equimolar ratio (1:1:1) or in an equimolar ratio.

Embodiment A.1. The three-component crystal of embodiment A, wherein the amine base is a pyridine base.

Embodiment A.2. The three-component crystal of embodiment A.1, wherein the pyridine base is 3-picoline.

Embodiment A.3. The three-component crystal of embodiment A.2 having unit cell dimensions of approximately 12.12 Å×15.80 Å×12.28 Å.

Embodiment B. A method for the preparation of a three-component crystal comprising a compound of Formula II, a compound of Formula III and an amine base in an approximately, or in an, equimolar ratio (1:1:1), the method comprising the steps of: (i) mixing the compound of Formula II, the compound of Formula III and the amine base in approximately equimolar amounts in a polar aprotic solvent, and (ii) isolating the three-component crystals from the polar aprotic solvent.

Embodiment B.1. The method of embodiment B, wherein the aprotic polar solvent is acetonitrile.

Embodiment B.2. The method of embodiment B or embodiment B.1, wherein the amine base is a pyridine base.

Embodiment B.3. The method of embodiment B.2, wherein the pyridine base is 3-picoline.

Embodiment C. A method for the preparation of a compound of Formula I, the method comprising the steps of (a) reacting a suspension of a three-component crystal comprising a compound of Formula II, a compound of Formula III and an amine base in an approximately, or in an, equimolar ratio (1:1:1) in an aprotic polar solvent with an acid activating agent, and (b) allowing the coupling of acid activated compounds of Formulas II and III to proceed to the formation of the compound of Formula I.

Embodiment C.1. The method of embodiment C, wherein the aprotic polar solvent is acetonitrile.

Embodiment C.2. The method of embodiment C or embodiment C.1, wherein the acid activating agent is a sulfonyl chloride, such as methane sulfonyl chloride.

Embodiment C.3. The method of embodiment C or embodiments C.1-C.2, wherein the amine base is a pyridine base, Embodiment C.4. The method of embodiment C.3, wherein the pyridine base is 3-picoline.

Embodiment D. A method for the preparation of a compound of Formula I, the method comprising the steps of (a)

preparing a mixture comprising a compound of Formula II, compound of Formula III, an amine base and a polar aprotic solvent, (b) gradually adding an acid activating agent to the mixture, and (c) allowing the coupling of acid activated compounds of Formulas II and III to proceed to the formation of the compound of Formula I, wherein seeding material of the compound of Formula I is (i) added when preparing the mixture of step (a); (ii) added to the mixture before the acid activating agent has been added in step (b); or (iii) added during addition of the activating agent in step (b).

Embodiment D.1. The method of embodiment D, wherein the amount of seeding material of the compound of Formula I is in the range of 0.5-15 mol-%.

Embodiment D.2. The method of embodiment D or embodiment D.1, wherein the mixture comprising the seeding material has a temperature in the range of from about 30° C. to reflux, or from about 40° C. to reflux or from about 45° C. to about 70° C.

Embodiment D.3. The method of embodiments D or embodiments D.1-D.2, wherein the seeding material of the compound of Formula I is added when preparing the mixture of step (a) or before addition of the activating agent in step (b).

Embodiment D.4. The method of embodiment D.3, wherein the amount of seeding material of the compound of Formula I is in the range of about 5-15 mol-%.

Embodiment D.5. The method of embodiments D or embodiments D.1-D.2, wherein the amount of seeding material of the compound of Formula I is added after addition of a part of the acid activating agent, such as at least about 5% of the acid activating agent, in step (b).

Embodiment D.6. The method of embodiment D.5, wherein the amount of seeding material of the compound of Formula I is in the range of about 0.5-5 mol-%.

Embodiment D.7. The method of embodiment D or embodiments D.1-D.6, wherein the aprotic polar solvent is acetonitrile.

Embodiment D.8. The method of embodiment D or embodiments D.1-D.7, wherein the acid activating agent is a sulfonyl chloride, such as methane sulfonyl chloride.

Embodiment D.9. The method of embodiment D or embodiments D.1-D.8, wherein the amine base is a pyridine base, such as 3-picoline.

Embodiment D.10. The method of embodiment D or embodiments D.1-D.9, wherein the seeding material of the compound of Formula I is in the form of purified crystalline material, centrifuged wet crystalline material, a suspension of solid material of Formula I in an organic solvent, or a non-quenched slurry of crystalline material from a previous reaction.

Of note is that compositions of this disclosure allow for the use of impure qualities of the compounds of Formulas II and III in the preparation of chlorantraniliprole. In some embodiments, the 1:1:1 crystals of embodiments A-C may be filtered and/or isolated, leaving all impurities in a mother liquor, and then reacted to produce clean chlorantraniliprole compounds. In some embodiments, high purity may be achieved with only one crystallization. In some embodiments, the 1:1:1 crystal may contain the exact stoichiometric amount of each intermediate needed for the reaction.

In some embodiments, generating a 1:1:1 crystal of embodiments A-C may help ensure that a reaction is run with the exact proportions of compounds of Formulas II and III needed to produce chlorantraniliprole, and may further allow the process to be run with better control.

In some embodiments, the use of 1:1:1 crystals of embodiments A-C promotes formation of smaller crystals of chlorantraniliprole. In some embodiments, the 1:1:1 crystals may act as a nucleation source during crystallization of the compound of Formula I. In some embodiments, the seeding material of embodiment D may lead to the formation of larger and more uniform crystals.

In various embodiments of embodiment D, the amount of seeding material of the compound of Formula I is added after addition of a part of the acid activating agent, such as at least about 5% of the acid activating agent, or about 10% to about 20% of the activating agent, or about 15% to about 20% of the activating agent, in step (b)

In various embodiments, suitable amine bases include tertiary amines (including optionally substituted pyridines) and mixtures thereof. In various embodiments, suitable amine bases may include 2-picoline, 3-picoline, 2,6-lutidine, pyridine and mixtures of the foregoing.

In various embodiments, suitable solvents include nitriles (e.g., acetonitrile, propionitrile), esters (e.g., methyl acetate, ethyl acetate, butyl acetate), ketones (e.g., acetone, methyl ethyl ketone, methyl butyl ketone, haloalkanes (e.g., dichloromethane, trichloromethane), ethers (e.g., ethyl ether, methyl tort-butyl ether, tetrahydrofuran, p-dioxane), aromatic hydrocarbons (e.g., benzene, toluene, chlorobenzene, dichlorobenzene), tertiary amines (e.g., trialkylamines, dialkylanilines, optionally substituted pyridines), and mixtures of the foregoing.

In various embodiments, the acid activating agent is used as a reactant to facilitate coupling of compounds of Formulas II and III. The nominal mole ratio of the acid activating agent to the compound of Formula II may be from about 1.0 to 2.5 or from 1.1 to 1.4. Suitable acid activating agents include sulfonyl chloride compounds such as methanesulfonyl chloride, propanesulfonyl chloride, benzenesulfonyl chloride, and 7-toluenesulfonyl chloride.

In various embodiments, the methods of the disclosure may be conducted over a wide range of temperatures, but commonly it is conducted at temperatures ranging from −70° C. to +100° C. or from 30° C. to reflux or from 40° C. to reflux or from 45° C. to 70° C. In some embodiments of embodiment D, the reaction is conducted at a temperature of about 50° C.

In various embodiments, the amount of seeding material of the compound of Formula I is in the range of 0.5-15 mol-%, or from 0.5-5 mol-% or from 5-10 mol-% or from 5-15 mol-%.

In various embodiments, the 1:1:1 crystal of the disclosure may include a three-component co-crystal containing a compound of Formula II, a compound of Formula III, and 3-picoline in an equimolar ratio. In some embodiments, the 3-picoline and the compound of Formula II may exist as a salt in the crystal. In one embodiment, the 1:1:1 crystal may appear with a monolithic structure, a density of 1.512-g/$cm^3$, and unit cell dimensions of 12.12 Å×15.80 Å×12.28 Å. In various embodiments, the 1:1:1 crystal may be characterized by a solubility, of between about 15 to 60 w/w % over a temperature range of 20 to 55° C.

The 1:1:1 crystal may be prepared by mixing 1-mol eq of the compound of Formula II, 1 mol-eq of the compound of Formula III and 1-mol eq of picoline in acetonitrile, and then adding seed crystals of the 1:1:1 crystal to the resulting supersaturated solution to initiate the crystallization. Alternatively, a reactor that has already produced the 1:1:1 crystal may be used to initiate crystallization without the use of seed crystals. Cooling, and/or addition of an antisolvent, may also be used to further drive the precipitation of the 1:1:1 crystal. The 1:1:1 crystal may then be recovered and used later in the process for preparing chlorantraniliprole. Suitable recovery processes include filtration and the like. The 1:1:1 crystal may also be reacted immediately, using standard quantities of methanesulfonyl chloride and picoline, to form chlorantraniliprole.

Comparative Example 1

Preparation of 3-bromo-N-[4-chloro-2-methyl-6-[(methylamino)carbonyl]phenyl]-1-(3-chloro-2-pyridinyl)-1H-pyrazole-5-carboxamide (chlorantraniliprole)

Acetonitrile (54.5 g), 3-bromo-1-(3-chloro-2-pyridirtyl)-1H-pyrazole-5-carboxylic acid (46.6 g, 0,15 mol), 2-amino-5-chloro-N,3-dimethylbeitzamide (32.1 g, 0.16 mol), and 3-picoline (37.3 (37.3 g, 0.40 mol) were mixed together at 20° C. in a jacketed, agitated vessel containing 1:1:1 seed crystals. The resulting mixture formed a crystal slurry of 1:1:1 in the vessel. Methanesulfonyl chloride (21.2 g, 0.19-mol) was then slowly added over 120 minutes, keeping the temperature around 32° C., and then the reaction was held for an additional 1 hour. Water (46 g) was then added to the reactor over a 60 minute period, and the mixture was held for an additional 1 hour. The resulting slurry was filtered and washed with a 5:1 acetonitrile and water mixture. Chlorantranili prole was produced with a >90% yield. The resulting median particle size was 16.3 μm.

Example 2

Preparation of 3-bromo-N-[4-chloro-2-methyl-6-[(methylamino)carbonyl]phenyl]-1-(3-chloro-2-pyridinyl)-1H-pyrazole-5-carboxamide (chlorantraniliprole)

3-bromo-1-(3-chloro-2-pyridinyl)-1H-pyrazole-5-carboxylic acid (46.6 g, 0.15 mol), 2-amino-5-chloro-N,3-dimethylbenzamide (30.6 g, 0.15 mol), and 3-picoline (14.3 g, 0.15 mol) are mixed together with an acetonitrile solution (58.6 g acetonitrile) saturated with 1:1:1 crystals at 20° C., in a jacketed, agitated vessel containing 1:1:1 seed crystals. The resulting slurry is filtered, and the 1:1:1 solids are washed with acetonitrile and dried.

1:1:1 crystals (91.5 g), acetonitrile (54.5 g) and 3-picoline (23.0 g) are mixed together at 20° C. in a jacketed, agitated vessel. Methanesulfonyl chloride (21.2 g, 0.19 mol) was then slowly added over 120 minutes, keeping the temperature around 32° C., and then the reaction is held for an additional 1 hour. Water (46 g) is then added to the reactor over a 60 minute period, and the mixture is held for an additional 1 hour. The resulting slurry was filtered and washed with a 5:1 acetonitrile and water mix, Chlorantraniliprole was produced with a >90% yield.

Example 3

Preparation of 3-bromo-N-[4-chloro-2-methyl-6-[(methylamino)carbonyl]phenyl]1-(3-chloro-2-pyridinyl)-1H-pyrazole-5-carboxamide (chlorantraniliprole)

3-bromo-1-(3-chloro-2-pyridinyl)-1114-pyrazole-5-carboxylic acid (583.0 g), 2-amino-5-chloro-N,3-dimethylbenzamide (406.5 g), chiorantraniliprole seeding material (94.5 g) and acetonitrile (684.9 g) were charged to a 3 L programmable heating/cooling device controlled jacketed reactor fitted with a thermometer, mechanical stirrer (two-by-two blade pitch-type), reflux condenser (fitted with nitrogen coverage/nitrogen bubbler) and syringe pump (programmable) inlet. Agitation was adjusted to 200 rpm. The mixture was heated to 50° C. 3-picoline (469.4 g) was added to the stirred mixture after the temperature had reached 40° C. during heating. A 50 mL syringe with MSC was charged and dosing started according to Table 1 below when the mixture had reached 50° C. (262.6 g in total).

TABLE 1

| Run time [min] | m(MSC) [g] | m(MSC) [mL] |
|---|---|---|
| 0 | 0.0 | 0.0 |
| 20 | 35.5 | 24.0 |
| 40 | 73.0 | 49.3 |
| 60 | 112.9 | 76.3 |
| 80 | 156.2 | 105.6 |
| 100 | 204.6 | 138.2 |
| 120 | 260.5 | 176.0 |
| 120.7 | 262.6 | 177.4 |

After MSC dosing was complete, the reaction was allowed to reach completion after another 1 h of post-reaction time. Water (577.5 g in total) was dosed according to the Table 2 below:

TABLE 2

| Run time [min] | m(Water) [g] |
|---|---|
| 0 | 0 |
| 60 | 143.9 |
| 120 | 431.6 |

The mixture was cooled to 20° C. over a period of 30 minutes, The suspension was transferred to a vacuum filter and vacuum was applied. After the filter cake settled, suction was continued for another 5 minutes, The filter cake was washed with water (767.3 g) and the wet cake was left on the filter with suction for another 30 minutes. The wet cake was dried at 50° C. under vacuum overnight.

The dried chlorantraniliprole crystals were then weighed out and samples taken for HPLC and solid state analyses.

Isolated Yield: 95-98% (seed corrected, based on 3-bromo-1-(3-chloro-2-pyridinyl)-1H-pyrazole-5-carboxylic acid)

Average purity: +97%

Crystal Size Distribution: D[4,3] values were in the range of 90-200 μm with only small amounts of fines Bulk Density: 0.62-0.70 g/mL (untapped); 0.75-0.80 g/mL (tapped)

Total dissolution of the 1:1:1 crystals was observed during the above reaction. The resulting chlorantraniliprole crystals were observed to be large and uniform, centrifuged extremely rapidly, dried quickly and provided a product with a large bulk density with minimal dust production.

Example 4

Preparation of 3-bromo-N-[4-chloro-2-methyl-6-[(methylamino)carbonyl]phenyl]-1-(3-chloro-2-pyridinyl)-1H-pyrazole-5-carboxamide (chlorantraniliprole)

Chlorantraniliprole crystals were prepared in Experiments 1-12 using the parameters in Tables 3-5 below. As can be observed in Table 4, increasing the stirring speed lead to a decrease in particle size and untapped bulk density.

TABLE 3

| Description | Exp 1 (MCh-20A) | Exp 2 (MCh-20B) | Exp 3 (MCh-26B) | Exp 4 (MCh-27B) |
|---|---|---|---|---|
| | 50° C. reaction temp (Non-quenched) | | Seeding at 16% MsCl addition | |
| 1:1:1 seeding | Yes | Yes | Yes | Yes |
| Chloran. seeding | No | Yes | No | Yes |
| Stir rate (rpm) | 300 | 300 | 300 | 300 |
| Scale (mmol) | 280 | 280 | 280 | 280 |
| Purity (%) | 89.3 | 86.9 | Not Run | Not Run |
| Yield (%) | 76.7 | 79 | Not Run | Not Run |
| Density (untapped) (g/mL) | Not Run | Not Run | Not Run | Not Run |
| Density (tapped) (g/mL) | Not Run | Not Run | Not Run | Not Run |
| CSD D[4,3] (μm) | 203.7 | 182.3 | 197 | Not Run |
| Impurity (%) | 6.07 | 7.98 | 2.21 | 8.80 |

TABLE 4

| Description | Exp 5 (MCh-31A) | Exp 6 (MCh-31B) | Exp 7 (MCh-35A) | Exp 8 (MCh-35B) |
|---|---|---|---|---|
| | 2 × 2 pitch blade stirrer | | Twisted 2-blade stirrer | |
| 1:1:1 seeding | Yes | No | Yes | Yes |
| Chloran. seeding | Yes | Yes | Yes | No |
| Stir rate (rpm) | 200 | 200 | 1200 | 1200 |
| Scale (mmol) | 2800 | 2800 | 280 | 280 |
| Purity (%) | 98.4 | 97.3 | 98.3 | 97.6 |
| Yield (%) | 97.3 | 95.4 | 96.7 | 95.3 |
| Density (untapped) (g/mL) | 0.69 | 0.71 | 0.66 | 0.64 |
| Density (tapped) (g/ml) | 0.76 | 0.82 | 0.83 | 0.79 |
| CSD D[4,3] (μm) | 128 | 218 | 91.2 | 82.6 |
| Impurity (%) | 1.60 | 1.84 | 1.75 | 1.87 |

TABLE 5

| Description | Exp 9 (MCh-42A) | Exp 10 (MCh-42B) | Exp 11 (JKV-31A) | Exp 12 (JKV-31B) |
|---|---|---|---|---|
| | 2 × 2 pitch blade stirrer | | MsCl exotherm heating to 50° C. | |
| 1:1:1 seeding | Yes | Yes | Yes | Yes |
| Chloran. seeding | No | Yes | Yes | No |
| Stir rate (rpm) | 500 | 500 | 500 | 500 |
| Scale (mmol) | 2800 | 2800 | 2800 | 2800 |
| Purity (%) | 97.8 | 99.0 | 99.5 | 97.2 |
| Yield (%) | 96.4 | 97.1 | 98.3 | 96.8 |
| Density (untapped) (g/mL) | 0.52 | 0.70 | 0.49 | 0.56 |
| Density (tapped) (g/mL) | 0.66 | 0.82 | 0.65 | 0.71 |
| CSD D[4,3] (μm) | 119 | 107-133 | 171.4 | 83.2 |
| Impurity (%) | 1.92 | 2.19 | 1.79 | 1.81 |

What is claimed is:

1. A solid three-component crystal, wherein the three components are:

(a) a compound of Formula II:

Formula II

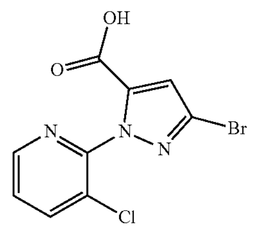

(b) a compound of Formula III; and

Formula III

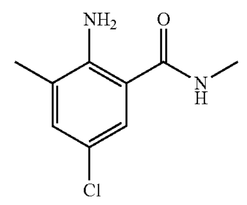

(c) an amine base, wherein the components are in an equimolar ratio of 1:1:1.

2. The three-component crystal of claim 1, wherein the amine is a pyridine base.

3. The three-component crystal of claim 1, wherein the pyridine base is 3-picoline.

4. The three-component crystal of claim 1, having unit cell dimensions of about 12.12 Å×about 15.80 Å×about 12.28 Å.

5. A method for the preparation of a solid three-component crystal, wherein the three components are:

(a) a compound of Formula II:

Formula II

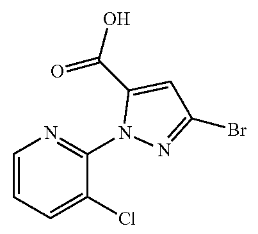

(b) a compound of Formula III; and

Formula III

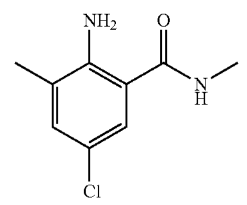

(c) an amine base, the method comprising the steps of:

(i) forming an admixture of the compound of Formula II, the compound of Formula III and the amine base in an equimolar amount of 1:1:1 in an aprotic solvent, (ii) forming the three-component crystals therefrom, and (iii) isolating the three-component crystals from the polar aprotic solvent.

6. The method of claim 5, wherein the aprotic solvent is acetonitrile.

7. The method of claim 5, wherein the amine base is a pyridine base.

* * * * *